United States Patent [19]

Bailey

[11] Plant 4,910

[45] Nov. 2, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,619

[22] Filed: Sep. 9, 1980

[51] Int. Cl.[3] ..... A01H 5/00

[52] U.S. Cl. ..... Plt./6

[58] Field of Search ..... Plt./6

*Primary Examiner*—James R. Feyrer

*Attorney, Agent, or Firm*—Vincent G. Gioia

[57] ABSTRACT

A new everblooming climbing rose variety of vibrant red flower coloring, and a vigorous plant with abundant foliage.

2 Drawing Figures

The present invention relates to a new and distinct variety of rose plant of the everblooming climbing rose class, which was originated by my crossing as seed parent the rose known as "Don Juan" and an unnamed, unreleased, unpatented seedling of my creation as pollen parent.

Among the novel characteristics possessed by this new variety which distinguish it from its parents and all other varieties of which I am aware are its continuous habit of blooming and its dense foliage, particularly at ground level to three to four feet from the ground. The blooming tends toward grandiflora characteristics with several good sized flowers borne in large sprays. Laterals of 6 to 8 feet are common and the plant is considered very hardy and disease resistant. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "46A" is plate 46A of the Royal Horticultural Society Color Chart.

Parentage: Seedling.

*Seed parent.*—"Don Juan".

*Pollen parent.*—Unnamed, unreleased seedling.

Class: Everblooming climber.

The following observations are made of specimens grown outdoors in Kern County, Calif. during the month of October.

1. FLOWER

Blooming habit: Continuous.

A. Bud:

(1) *Size.*—Small to medium.

(2) *Form.*—Ovoid.

(3) *Color.*—When sepals first divide — garnet red 60A. When petals begin to unfurl — 46A to 46B.

(4) *Sepals.*—Short, pointed, extending ½ length of bud.

(5) *Peduncle.*—Length — short. Aspect — straight. Strength — erect. Color — 147A with deep purple red shading.

B. Bloom:

(1) *Size.*—Average size when fully expanded — about 3 to 3½ inches.

(2) *Borne.*—Several together in sprays.

(3) *Form.*—Flat, becoming ruffled at maturity.

(4) *Petalage.*—Number of petals under normal conditions — about 37.

(5) *Color.*—Petal coloring tends to 60A with inner petals 53B and outer petals 60A. The general tonality from a distance is Cardinal red 53A with overtones of 60A at edges of inner petals when flowers are fully open. There is seemingly little change in color as blooms age but general tonality may vary between 53D and 46A lightening to 45A after several days.

C. Petals:

(1) *Texture.*—Thick.

(2) *Appearance.*—Velvety to satiny.

(3) *Form.*—Short, rounded.

(4) *Arrangement.*—Regularly arranged shingle-like.

(5) *Petaloids in center.*—Few.

(6) *Persistence.*—Drop off cleanly.

(7) *Fragrance.*—Moderate old rose.

(8) *Lasting quality.*—Long lasting on plant and as cut flower e.g. 5 to 6 days.

2. REPRODUCTIVE ORGANS

A. Stamens, filaments and anthers:

(1) *Arrangement.*—Regular, around styles.

(2) *Color.*—14C.

B. Pollen:

*Color.*—17B.

C. Styles: Short, bunched.

D. Stigmas:

*Color.*—22A.

E. Hips:

*Shape.*—Globular.

*Size.*—Medium to large.

*Color.*—Reddish orange.

*Do seeds protrude?* — No.

3. PLANT

A. Form: Upright.

B. Growth: Very vigorous, uniform branching, long lasting canes.

*Height attained.*—About 6 to 8 feet.

C. Foliage: Compound 5 to 7 leaflets.

(1) *Size.*—Large.

(2) *Quantity.*—Abundant, dense, especially at ground level.

(3) *Color.*—New foliage: upper side — near to 146A. Under side — near to 146C. Old foliage: upper side — near 137A. Under side — near 146B.

(4) *Shape.*—Long pointed.

(5) *Texture.*—Upper side is thick, waxy and under side is dull, smooth.

(6) *Edge.*—Almost smooth.

(7) *Serration.*—Small serration at tip or point of leaflet.

(8) *Leaf stem.*—Color — near to 137D. Under side — near 146C.

(9) *Stipules.*—Medium length, slightly bearded.

(10) *Resistance to disease.*—Blackspot — excellent. Mildew — excellent. Rust — excellent.

D. Wood:

(1) *New wood.*—Color — light bronze green. Bark — smooth, slightly wavy.

(2) *Old wood.*—Color — reddish green. Bark — smooth, with some twisting.

E. Thorns:

(1) *Thorns.*—Quantity (main stalk) — ordinary. On laterals from stalk — abundant. Form — flat and straight. Length — medium. Color — pale red green. Position — regular.

(2) *Prickles.*—Normal, profuse near blooms.

F. Winter hardiness: Good winter hardiness.

I claim:

1. A new and distinct variety of rose plant of the everblooming climber class, substantially as shown and described, characterized particularly by continuous blooming habit and dense foliage, particularly at ground level, and bright red flowers borne several together in sprays and long strong laterals.

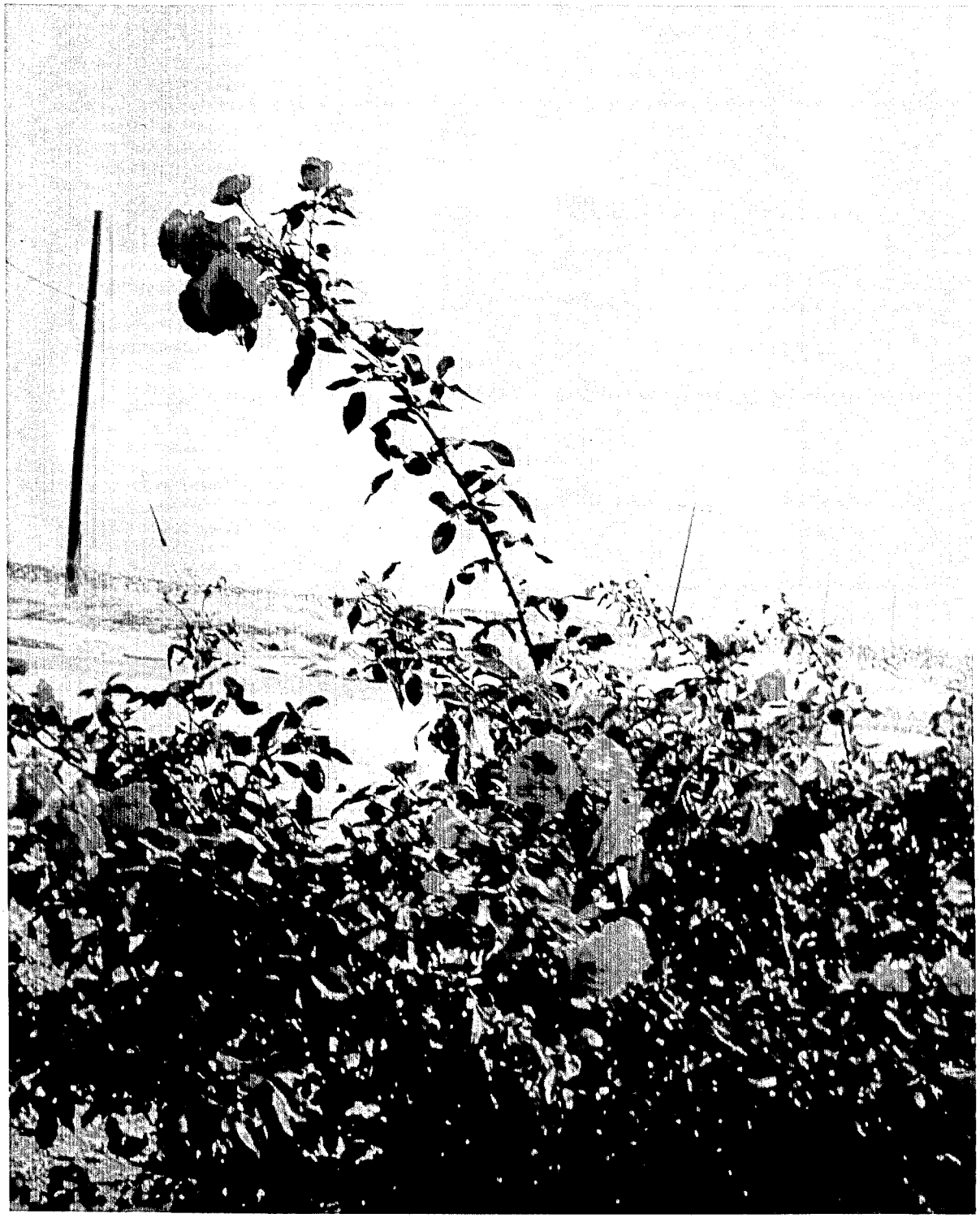

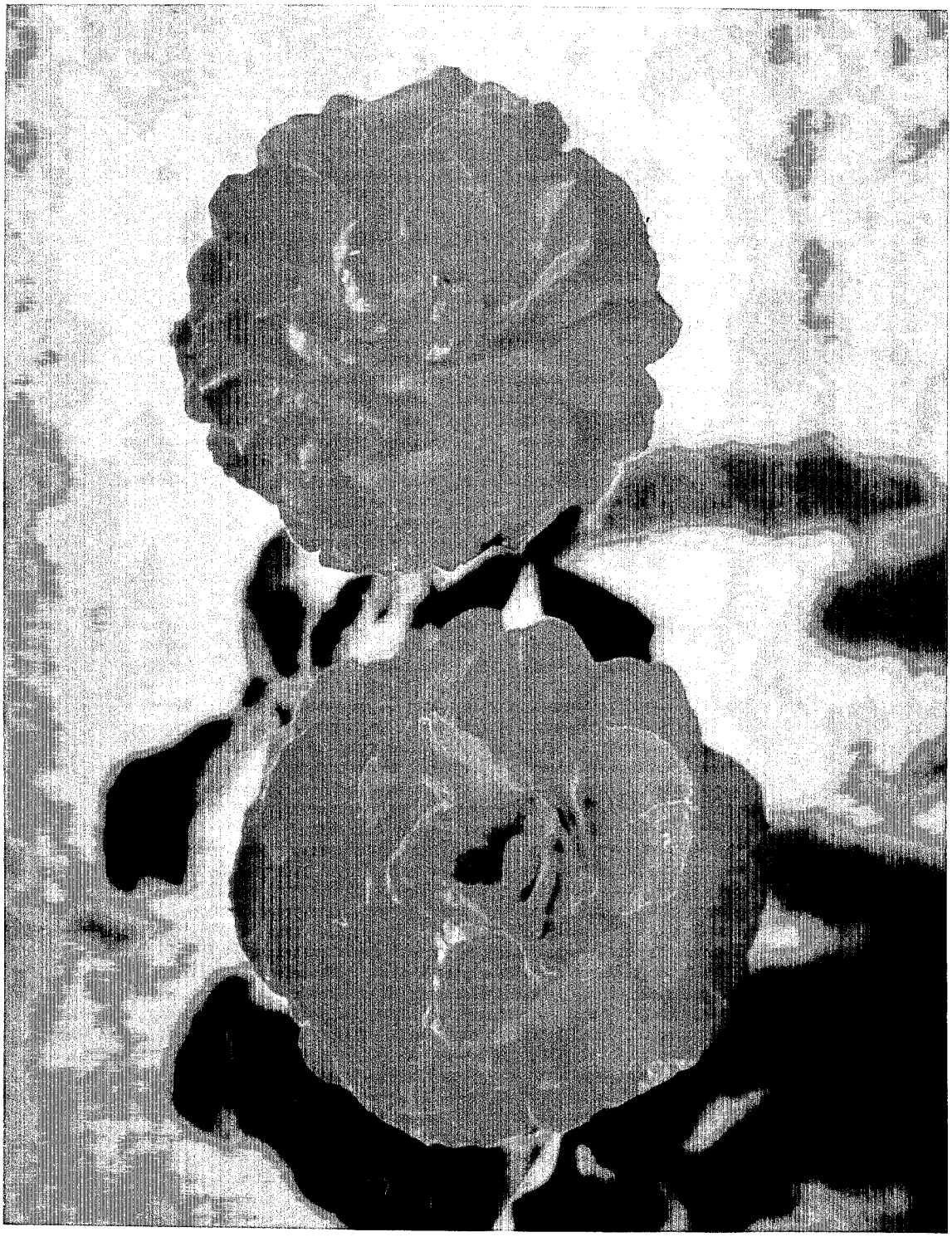

* * * * *